United States Patent
Duelo Riu et al.

(10) Patent No.: US 9,795,654 B2
(45) Date of Patent: *Oct. 24, 2017

(54) DIAMINE OXIDASE FOR USE IN THE TREATMENT OR PREVENTION OF ATTENTION DEFICIT HYPERACTIVITY DISORDER (ADHD)

(71) Applicant: DR HEALTHCARE ESPAÑA, S.L., Barcelona (ES)

(72) Inventors: Carlos Duelo Riu, Barcelona (ES); Juan José Duelo Riu, Barcelona (ES)

(73) Assignee: DR HEALTHCARE ESPAÑA, S.L., Barcelona (ES)

( * ) Notice: Subject to any disclaimer, the term of this patent is extended or adjusted under 35 U.S.C. 154(b) by 73 days.

This patent is subject to a terminal disclaimer.

(21) Appl. No.: 14/394,589

(22) PCT Filed: Apr. 18, 2013

(86) PCT No.: PCT/IB2013/053068
§ 371 (c)(1),
(2) Date: Oct. 15, 2014

(87) PCT Pub. No.: WO2013/156955
PCT Pub. Date: Oct. 24, 2013

(65) Prior Publication Data
US 2015/0093430 A1    Apr. 2, 2015

(30) Foreign Application Priority Data
Apr. 18, 2012    (ES) .................................. 201230578

(51) Int. Cl.
| *A61K 38/44* | (2006.01) |
| *A61K 9/16* | (2006.01) |
| *A61K 9/48* | (2006.01) |
| *A61K 9/50* | (2006.01) |
| *A61K 31/522* | (2006.01) |
| *C12N 9/06* | (2006.01) |

(52) U.S. Cl.
CPC ............... *A61K 38/44* (2013.01); *A61K 9/16* (2013.01); *A61K 9/48* (2013.01); *A61K 9/50* (2013.01); *A61K 31/522* (2013.01); *C12N 9/0022* (2013.01); *C12Y 104/03006* (2013.01)

(58) Field of Classification Search
CPC ............ A23V 2002/00; A23V 2200/31; A23V 2200/3204; A23V 2200/322; A23V 2250/032; A23V 2250/161; A23V 2250/1882; A23V 2250/51084; A23V 2250/51086; A23V 2250/6418; A23V 2250/718; A61K 38/44; A61K 47/14; A61K 47/24; A61K 9/0014; A61K 9/0095; A61K 9/1623; A61K 9/48; A61K 47/10; A61K 47/26; A61K 47/32; A61K 47/44; A61K 9/00; A61K 9/06; A61K 9/107; A61K 9/16; A61K 9/2018; A61K 9/50; A61K 9/5026; A61K 9/5047; A61K 9/703; A61K 9/7046; C12Y 104/03022; C12Y 104/03006; A23L 33/17; A23L 2/02; A23L 2/52; A23L 33/115; A23L 1/3053; A23L 33/10; A23L 33/18; C12N 9/0022; A23C 11/103; A23C 2210/40; A23C 9/1213; A23P 10/28; A23P 10/30; A23P 10/40; A61H 2201/165; A61H 2201/168; A61H 2205/028; A61H 39/04; A61H 7/006
See application file for complete search history.

(56) References Cited

U.S. PATENT DOCUMENTS

| 3,721,733 A | 3/1973 | Van Leeuwen |
| 4,703,045 A | 10/1987 | Guinot |
| 4,725,540 A | 2/1988 | Underberg et al. |
| 4,851,243 A | 7/1989 | Andersen et al. |
| 8,003,343 B2 | 8/2011 | Missbichler et al. |
| 2006/0002913 A1 | 1/2006 | Gehlsen |
| 2008/0193491 A1* | 8/2008 | Missbichler ............ A23L 1/034 424/401 |
| 2008/0227116 A1 | 9/2008 | Missbichler et al. |
| 2008/0306066 A1* | 12/2008 | Carruthers ........... C07D 213/38 514/235.8 |
| 2010/0330191 A1 | 12/2010 | Missbichler et al. |
| 2011/0236491 A1 | 9/2011 | Chantalat et al. |
| 2013/0344136 A1 | 12/2013 | Duelo Riu et al. |
| 2013/0344137 A1 | 12/2013 | Duelo Riu et al. |
| 2014/0004179 A1 | 1/2014 | Duelo Riu et al. |
| 2014/0004180 A1 | 1/2014 | Duelo Riu et al. |
| 2016/0024481 A1 | 1/2016 | Duelo Riu et al. |
| 2017/0020993 A1 | 1/2017 | Duelo Riu et al. |

FOREIGN PATENT DOCUMENTS

| EP | 0132674 A2 | 2/1985 |
| EP | 0865737 A2 | 9/1998 |
| EP | 1277477 A2 | 1/2003 |
| EP | 2020446 A1 | 2/2009 |
| ES | 2132037 A1 | 8/1999 |

(Continued)

OTHER PUBLICATIONS

Stevenson et al. (2010) Am J Psychiatry 167: 1108-1115.*
Cozza, S.J. et al.; "Treatment of Children and Adolescents"; Clinical Psychiatric Treatment, vol. II, Chapter XXXIII; 2004; p. 1408.
Stoltner, Anton, "International Search Report," prepared for PCT/IB2013/053068, as mailed Aug. 13, 2013, four pages.
Wigal, Sharon B.; "Efficacy and Safety Limitations of Attention-Deficit Hyperactivity Disorder Pharmacotherapy in Children and Adults"; CNS Drugs 2009; 23 Suppl. 1, 2009; pp. 21-31.
Brown, Ronald T. et al.; "Treatment of Attention-Deficit/Hyperactivity Disorder: Overview of the Evidence"; Pediatrics vol. 115, No. 6; Jun. 6, 2005; pp. e749-e757.

(Continued)

*Primary Examiner* — Lisa J Hobbs
(74) *Attorney, Agent, or Firm* — Winstead PC

(57) ABSTRACT

The present invention refers to diamine oxidase for use in the treatment or prevention of attention deficit hyperactivity disorder (ADHD).

10 Claims, No Drawings

(56) References Cited

FOREIGN PATENT DOCUMENTS

| | | | |
|---|---|---|---|
| ES | 2387973 | B1 | 10/2013 |
| ES | 2388395 | B1 | 10/2013 |
| ES | 2388515 | B1 | 10/2013 |
| FR | 2101095 | A1 | 3/1972 |
| FR | 2215944 | A1 | 8/1974 |
| GB | 1313318 | A | 4/1973 |
| WO | WO-9207475 | A1 | 5/1992 |
| WO | WO-9631130 | A2 | 10/1996 |
| WO | WO-0243745 | A2 | 6/2002 |
| WO | WO-03/035000 | A2 | 5/2003 |
| WO | WO-2006003213 | A1 | 1/2006 |
| WO | WO-2007/144153 | A2 | 12/2007 |
| WO | WO-2008/113871 | A1 | 9/2008 |
| WO | WO-2012127381 | A1 | 9/2012 |
| WO | WO-2012127391 | A1 | 9/2012 |
| WO | WO-2012127392 | A1 | 9/2012 |

OTHER PUBLICATIONS

Montañés-Rada, F. et al.; "Fármacos para el trastorno por déficit de atención/hiperactividad"; Rev Neurol 2009; 48(9); Mar. 31, 2009; pp. 469-481.

Howard, Harry R.; "Agents for Attention-Deficit Hyperactivity Disorder—an Update"; Expert Opinion on Therapeutic Patents, Informa Healthcare, GB; vol. 14, No. 7; Jul. 1, 2004; pp. 983-1008.

U.S. Appl. No. 14/871,694, Duelo Riu et al.

U.S. Appl. No. 15/283,778, Duelo Riu et al.

Tallgren, Antti, "International Search Report" prepared for PCT/IB2012/051276, as mailed Jun. 9, 2012, 6 pages.

Tallgren, Antti,"International Search Report", prepared for PCT/IB32012/051253 as mailed Jul. 6, 2012, 4 pages.

Tallgren, Antti, "International Search Report" for PCT/IB2012/051252, as mailed Jul. 6, 2012, 4 pages.

Maintz, Laura, et al., "Histamine and histamine intolerance", the American Journal of Clinical Nutrition, American Society for Nutrition, U.S., May 1, 2007, vol. 85, No. 5, pp. 1185-1196.

Zimmerman, "Pathophysiological Mechanisms of Fibromyalgia," the Clinical Journal of Pain, vol. 7, No. 1, pp. S8-S15, (1991).

Meggs, "Neurogenic Switching: A Hypothesis for a Mechanism for Shifting the Site of Inflammation in Allergy and Chemical Sensitivity Environmental Health Perspectives," vol. 103, No. 1, pp. 54-56, (1995).

Arnold et al., "Family Study of Fibromyalgia," Arthritis & Rheumatism, vol. 50, No. 3, pp. 944-952, (2004).

Van Ittersum et al., "Illness Perceptions in Patients with Fibromyalgia," Patient Education and Counseling, vol. 74, Issue 1, pp. 53-60, (2009).

Mason et al., "Evaluation of a Multimodal Treatment Program for Fibromyalgia," Journal of Behavioral Medicine, vol. 21, No. 2, pp. 163-178, (1998).

Vaerøy et al., "Treatment of Fibromyalgia (Fibrositis Syndrome): A Parallel Double Blind Trial with Carisoprodol, Paracetamol and Caffeine (Somadril Comp®) Versus Placebo," Clinical Rheumatology, vol. 8, Issue 2, pp. 245-250, (1989).

Biofunctionalism.com, "Fibromyalgia and DAO Deficiency," http://biofunctionalism.com/fibromyalgia-and-dao-deficiency/, Oct. 11, 2010, 3 pages.

Dechene, L.; "Chronic Fatigue Syndrome: Influence of Histamine, Hormones and Electrolytes"; Medical Hypothesis, vol. 40, No. 1; Jul. 1992; pp. 55-60.

John, Joshi, et al.; "Caffeine Promotes Glutamate and Histamine Release in the Posterior Hypothalamus"; Am J Physiol Regul Integr Comp Physiol, vol. 307; Jul. 16, 2014; pp. R704-R710.

Grozman, M., et al.; "Change in Serum Histamine Indexes in Calves under the Influence of Caffeine"; Trudy Moldayskoi Ovoshchekartofel'noi Orositel'noi Opytnoi Stantsii (1971), 7, 277-80 (Abstract only).

Roth, J.A., et al.; "The Effect of Vagotomy and Atropine upon Caffeine Stimulation of Gastric Secretion"; Gastroenterology (1945), 5, 129-34 (Abstract only).

Bodmer, S., et al.; "Biogenic Amines in Foods: Histamines and Food Processing"; Inflammation Research, vol. 48, No. 6; Jun. 1999; pp. 296-300.

Stoltner, Anton, "International Search Report" for PCT/IB2012/051275, as mailed May 21, 2012, 3 pages.

Shimoda, et al., "Investigation of the mechanism of alcohol-induced bronchial asthma", Journal of Allergy and Clinical Immunology, Mosby, Inc, US, Jan. 1, 1996, vol. 97, No. 1, pp. 74-84.

Linneberg, A., et al., "Genetic determinants of both ethanol and acetaldehyde metabolism influence alcohol hypersensitivity and drinking behaviour among Scandinavians", Clinical & Experimental Allergy, Wiley Interscience, Jan. 1, 2010, vol. 40, No. 1, pp. 123-130.

Pittler, Max H., et al.; "Interventions for Preventing or Treating Alcohol Hangover: Systematic Review of Randomised Controlled Trials"; BJM, vol. 331; Dec. 22, 2005; 4 pages.

Stephens, Richard, et al.; "A Review of the Literature on the Cognitive Effects of Alcohol Hangover"; Alcohol & Alcoholism, vol. 43, No. 2; Jan. 31, 2008; pp. 163-170.

Swift, Robert, et al.; "Alcohol Hangover: Mechanisms and Mediators"; Alcohol Health & Research World, vol. 22, No. 1; Jan. 1998; pp. 54-60.

\* cited by examiner

DIAMINE OXIDASE FOR USE IN THE TREATMENT OR PREVENTION OF ATTENTION DEFICIT HYPERACTIVITY DISORDER (ADHD)

FIELD OF THE INVENTION

The present invention relates to diamine oxidase (DAO) for use in the treatment or prevention of attention deficit hyperactivity disorder (ADHD).

BACKGROUND OF THE INVENTION

Attention deficit hyperactivity disorder (ADHD) is a disorder especially prevalent in children and is associated with an increase in motor activity and a reduction in attention. It is a behavioural syndrome with a neurological base and a strong genetic component. It is a very prevalent disorder affecting between 5% and 10% of the infant-juvenile population, being 3 times more frequent in males. No differences have been demonstrated between geographic areas, cultural groups or socio-economic levels. It represents between 20% and 40% of referrals to infant-juvenile psychiatric services.

This is a neurological disorder of behaviour characterised by moderate or severe distraction, short attention span, restlessness, emotional instability and impulsive behaviours. Although it was initially recognised in childhood, it has been recognised to have a chronic nature since it persists and manifests beyond adolescence. Long term studies have demonstrated that between 60% and 75% of children with ADHD continue to present symptoms in adult life.

The main traits of ADHD are firstly difficulty in maintaining concentration (attention deficit), especially in circumstances of low stimulation and secondly lack of inhibition or cognitive control over impulses, frequently associated with motor restlessness (hyperactivity-impulsiveness). These two sets of signs can appear separately or together.

The symptoms of ADHD fall into three groups:
Lack of attention (inattention)
Hyperactivity
Impulsive behaviour (impulsiveness)

Some children with ADHD have the type of disorder with mainly lack of attention. Others can have a combination of various types. Those children with the lack of attention type of disorder are less disturbed and they are less likely to be diagnosed with ADHD.

The symptoms of lack of attention are:
Not paying careful attention to details or making errors due to carelessness in school work.
Having difficulty in maintaining attention in tasks or games.
Not seeming to listen when talked to directly.
Not following instructions and not finishing school work, homework or other obligations at work.
Having difficulty in organising tasks and activities.
Avoiding or not wanting to commit to tasks that require continuous mental effort (such as school work).
Frequently losing toys, school work, pencils, books or tools necessary for tasks and activities.
Being easily distracted.
Often seeing to be forgetful in daily activities
The symptoms of hyperactivity are:
Playing with hands or feet and fidgeting when seated.
Leaving the chair when expected to remain seated.
Excessive running and climbing in inappropriate situations.
Having difficulty in playing quietly.
Often talking too much, always "on the go" or acting as if "driven by an engine".
The symptoms of impulsiveness are:
Replying before hearing the whole question.
Having difficulty in waiting their turn.
Butting in or interrupting others (disrupting conversations or games).

Too often, difficult children are incorrectly classified as children suffering attention deficit hyperactivity disorder and on the other hand, many children with the disorder remain undiagnosed. In either case, they often have much difficulty with learning and mood swings. The American Academy of Pediatrics (AAP) has published guidelines to help to clarify the matter.

The diagnosis is based on very specific symptoms that must be present in more than one scenario:
Children must have at least 6 symptoms of attention deficit or 6 symptoms of hyperactivity and impulsiveness, with some symptoms present before the age of 7.
The symptoms must be present for at least 6 months, be observed in two or more scenarios and not be caused by another problem.
The symptoms must be so serious that they cause significant difficulty in many scenarios, including in the home, school and relations with friends.

In older children, ADHD is in partial remission when there are still symptoms, but then it does not meet the complete definition of the disorder.

The child must be submitted to an evaluation by a doctor if suspected to have ADHD and this may include:
Questionnaires for the parents and teachers (for example, Connors, Burks).
Psychological evaluation of the child and the family, including an intelligence quotient test and psychological tests.
Mental, nutritional, physical, psycho-social and comprehensive development evaluation.

At the moment, there are no laboratory tests that have been established as diagnostic in the clinical assessment of attention deficit hyperactivity disorder.

Depression, lack of sleep, learning difficulties, tics and behavioural problems may be confused with, or appear along with ADHD. When children are suspected of suffering from this disorder, they must be carefully examined by a doctor to rule out other possible conditions or reasons for their behaviour.

The symptoms of ADHD express a biological problem and is currently dealt with by pharmacological treatment, which is still the most important therapeutic approach. Common treatments are paradoxically based on stimulants, which have been observed to improve symptoms. Among them are caffeine and nicotine, which are sometimes used by adolescents and adults for self-medication. The first report endorsing the use of psychostimulants, dating back to 1937, is when Charles Bradley established the efficacy and safety of amphetamine sulphate to treat hyperactive children.

Currently, the most widely used substances in the United States are methylphenidate (active ingredient behind the Ritalin trade name) and DL-amphetamine (Adderall), followed by dexamphetamine (Dexedrine) and methamphetamine. Other second line psychostimulants for ADHD treatment are pemoline (Cylert) and modafinil (Modiodal). In recent years, the drugs with immediate effect tend to be replaced by other preparations that, using the same active ingredients, achieve a longer lasting effect, improving the children's quality of life, especially schoolchildren. The use of many of these drugs has been questioned due to the side effects that occur.

Although stimulants are the first line therapy for this disorder, some antidepressants such as fluoxetine (Prozac), bupropion (Wellbutrin), venlafaxine (Effexor) and desipramine have shown some value, especially when ADHD occurs with co-morbidities such as major depressive disorder or anxiety disorders (for example generalised anxiety disorder).

Clinical investigations are under way seeking to extend the application of adrenergic active ingredients, non-stimulants, such as atomoxetine (Strattera, a synaptic norepinephrine reuptake inhibitor) and alpha-adrenergic agonists such as clonidine and guanfacine. Of these three, only atomoxetine has been approved for this indication. Launched in 2002, atomoxetine is proposed as a second-line drug when stimulants are not well tolerated. Treatment success rate does not exceed that of traditional drugs. Neither does it have a very benign side effect profile. Being a new substance, complete information regarding the expected long term effects are lacking. Recently, atomoxetine has been related to increased risks of liver toxicity, although the evidence for this is preliminary. Added to this, on 28 Sep. 2005, a warning was given by the Health Agency of Canada linking the use of this drug with possible phenomena of depersonalisation, self-harm and suicidal thoughts among adult and paediatric patients.

As with other psycho-pathologies where the treatment is predominantly pharmacological, both the diagnosis of ADHD and the viability of medical treatment have been openly rejected by supporters of the so-called anti-psychiatry movement.

Psychological treatment of associated behavioural problems is also accepted. These types of interventions are complementary to pharmacological treatment and normally seek to reduce disruptive behaviours of children in various environments by cognitive-behavioural type therapies. Similarly, educational psychology counselling may be advisable for learning difficulties that often appear in a large proportion of subjects with ADHD. Currently, positive development therapies are being developed in children, trying to reinforce the potential of young people through sport and group dynamics. Various researchers have developed reinforcement models through token economies with groups of children with ADHD and have shown that when well conducted, they give better results than individual therapy. In this way, aspects such as self-esteem and social skills can be explored.

Histamine [2-(4-Imidazolyl)ethylamine] is an important mediator of many biological processes including inflammation, gastric acid secretion, neuromodulation and regulation of the immune function. Because of its strong pharmacological activity, even at very low concentrations, synthesis, transport, storage, release and degradation of histamine must be very carefully controlled to prevent undesirable reactions. High concentrations of free histamine in circulation have been described to trigger unwanted effects such as headaches, stuffy or runny nose, respiratory tract obstructions, tachycardia, gastric and intestinal ailments, swelling of eyelids, skin rashes, reduced blood pressure, bronchospasm, etc.

Histamine is produced by the human body and stored in an inactive form in the metachromatic granules of mast cells and basophilic leukocytes, where it is available for immediate release. The highest histamine concentrations are measured in the lungs. After release, histamine is an extraordinarily strong mediator in a wide range of physiological and pathophysiological processes, frequently via interaction with cytokines.

Histamine can also enter the human body from the outside as it is generated by microbiological action in the course of processing foods and therefore is present in substantial amounts in many foods and fermented drinks such as wine, champagne and a large proportion of alcoholic drinks.

The main route of inactivation of ingested histamine is oxidative deamination of the primary amine group, catalysed by diamine oxidase (DAO), to give imidazole acetaldehyde.

The main function of DAO is to prevent histamine ingested through food from reaching the bloodstream via the intestine.

In addition to histamine, DAO can degrade other biogenic amines such as, for example, putrescine, spermidine and cadaverine. Its molecular weight is approximately 182 kDa with a carbohydrate proportion of 11%. It belongs to the class of amine oxidases that contain copper and catalyse oxidative deamination of primary amines to give aldehydes, ammonia and hydrogen peroxide. DAO uses molecular oxygen to oxidatively deaminate histamine to imidazole acetaldehyde, ammonia and hydrogen peroxide.

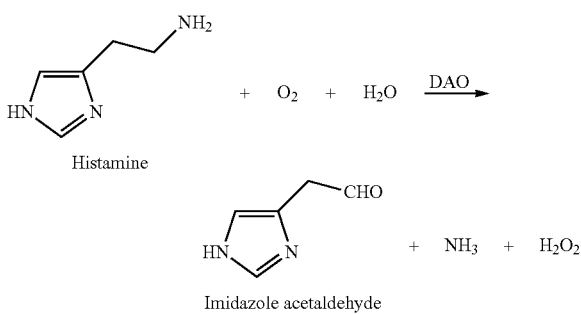

DAO is mainly found in the small intestine, liver, kidneys and blood leukocytes. Pregnant women have a blood DAO level of about 500 to 1000 times higher than non-pregnant women because DAO is also formed in the placenta. Histamine is continuously formed in the human body and excreted via the intestine, where it is degraded while passing through the intestinal mucosa by the DAO that is found there.

DAO is a sensitive enzyme that can be inhibited by various substances such as other biogenic amines, alcohol and by the degradation product acetaldehyde, and also by various medicines.

Apart from inhibition of DAO by certain types of substances, there is a significant percentage of the population whose blood DAO levels are abnormally low, which means that their blood histamine level is higher than values considered normal (2-20 micrograms/0.1 L). The high blood histamine levels in these types of subjects trigger a series of pathologies.

In this situation, preventative administration and treatment with supplementary DAO has the effect of contributing to degradation of excess histamine.

The present inventors have carried out clinical trials showing that treatment with supplementary DAO, which contributes to degradation of excess histamine, is very useful in the treatment or prevention of fibromyalgia or chronic fatigue (application ES 201130383), for blocking the effects of histamine release caused by consumption of alcoholic drinks and so preventing hangover symptoms (application ES 201130380) and for the treatment or prevention of diseases and pathological states associated with an elevated level of blood histamine that bring about an increase in pain, particularly in the treatment or prevention of migraine, fibromyalgia, spondylitis and muscle contractions (application 201130381).

The present inventors have found that approximately 80% of children with ADHD also show a congenital DAO activity deficiency, so they insufficiently metabolise ingested histamine, which passes to the blood. The problem is worsened by the fact that the majority of drugs that are prescribed in the treatment of ADHD are inhibitors of DAO activity. In principle these drugs improve the symptoms but in the long term the symptoms become chronic and create a dependency and requirement for higher doses, as the higher the medication the more DAO inhibition and more histamine passes into the bloodstream. Administration of DAO in children diagnosed with ADHD and DAO deficiency has been demonstrated to provide a significant improvement in the symptoms of attention deficit hyperactivity disorder.

U.S. Pat. No. 4,725,540 describes a method for the preparation of DAO from a DAO-producing microorganism such as *Candida krusei* or from a lactic acid producing bacterium in a nutrient medium, so that the DAO produced is able to degrade histamine at a pH of between neutral and approximately pH 4.

Patent application WO 02/43745 from 2001 describes the systemic use of DAO of vegetable origin for the treatment of diseases mediated by histamine, particularly for the treatment of allergies in general and anaphylactic reactions in particular. Pharmaceutical compositions comprising DAO as an active ingredient have also been described together with the corresponding doses and administration protocols. The DAO used is of plant origin. There has been no mention of the possible use of DAO compositions for the treatment or prevention of attention deficit hyperactivity disorder (ADHD).

Patent application WO 2006003213 from 2005 refers to pharmaceutical compositions for the treatment of diseases induced by histamine that comprise DAO of animal origin, presenting a composition for oral or peroral administration in an administration form protected against gastric acid. The compositions are particularly directed to the treatment of urticaria, atopic dermatitis and scombroid toxicity. In this patent application, the use of DAO of non-plant origin was preferred with the justification that this has the advantage that the allergens present in plants do not negatively influence the administration of this DAO because allergens essentially promote the release of endogenous histamine. The DAO used was preferably obtained from pig kidneys or by recombinant techniques. There has been no mention of the possible use of DAO compositions for the treatment or prevention of attention deficit hyperactivity disorder (ADHD).

Definitions

"DAO" is the abbreviation used to designate the enzyme diamine oxidase responsible for the catalysis of the oxidative deamination of the primary amine group of histamine to give imidazole acetaldehyde. It is responsible for the main histamine inactivation pathway.

"Attention deficit hyperactivity disorder (ADHD)" is a group of symptoms that are fundamentally characterised by:

Lack of attention (inattention)
Hyperactivity
Impulsive behaviour (impulsiveness).

"Non-plant origin" means any DAO that is not obtained from plants but from animal organisms or other non-plant organisms. Thus, this definition includes all DAO isolated from living creatures that are not plants.

"Plant origin" means any DAO obtained from plant organisms.

"Biotechnological origin" means any DAO prepared from recombinant cell cultures or in non-plant organisms of any type after isolating the DNA for DAO.

"Prevention" is understood to mean avoiding the appearance of symptoms that involve lack of attention, hyperactivity and impulsive behaviour.

"Treatment" is understood to mean clinical intervention in an attempt to change the natural development of attention deficit hyperactivity disorder.

Accordingly, the term "prevention or treatment of attention deficit hyperactivity disorder (ADHD)" is understood to mean avoiding the appearance of symptoms that involve lack of attention, hyperactivity and impulsive behaviour which characterised the ADHD as well as the clinical intervention in an attempt to change the natural development of attention deficit hyperactivity disorder characterised by said symptoms.

SUMMARY OF THE INVENTION

The problem to be solved by the present invention is the treatment and prevention of the symptoms associated with attention deficit hyperactivity disorder in the infant-juvenile population.

Until the present invention, the relation between the symptoms of attention deficit hyperactivity disorder and the accumulation of histamine had not been described and therefore it has never been proposed to influence these symptoms by treatment with DAO. The surprising effect of the present invention is that with the administration of DAO the blood histamine concentration reduces and this is associated with a significant improvement in the symptoms of attention deficit hyperactivity disorder.

The first aspect of the present invention relates to the use of DAO for the preparation of a composition for the prevention or treatment of attention deficit hyperactivity disorder (ADHD), and to diamine oxidase (DAO) for use in the treatment or prevention of attention deficit hyperactivity disorder (ADHD), as well as to a composition comprising DAO for use in the prevention or treatment of attention deficit hyperactivity disorder (ADHD)

The second aspect of the present invention is the use of DAO associated with caffeine in a composition for use in the prevention or treatment of attention deficit hyperactivity disorder, and to diamine oxidase (DAO) for use associated with caffeine in the treatment or prevention of attention deficit hyperactivity disorder (ADHD) and also to a composition that in addition to DAO comprises caffeine for use in the prevention or treatment of attention deficit hyperactivity disorder.

The third aspect of the present invention are oral formulations of DAO, optionally containing caffeine, in the form of tablets, capsules and sachets, as well as compositions comprising thereof.

The fourth aspect of the present invention are oral formulations of DAO, prepared from DAO in free form, in powder, lyophilised powder, microcapsules, nanocapsules or liposomes containing DAO and optionally caffeine, as well as compositions comprising thereof.

The fifth aspect of the present invention are oral formulations of DAO, prepared from DAO in free form, in powder, lyophilised powder, microcapsules, nanocapsules or liposomes with gastric protection containing DAO and optionally caffeine, as well as compositions comprising thereof.

DETAILED DESCRIPTION OF THE INVENTION

The first aspect of the present invention relates to the use of DAO for the preparation of a composition for the prevention or treatment of attention deficit hyperactivity disorder (ADHD), and to diamine oxidase (DAO) for use in the treatment or prevention of attention deficit hyperactivity disorder (ADHD), as well as to a composition comprising DAO for use in the prevention or treatment of attention deficit hyperactivity disorder (ADHD).

The origin of the DAO used in the present invention can be biotechnological or from animal or plant extraction.

When the DAO used is of non-plant origin, it will preferably be in the form of lyophilised powder. When the DAO used is of plant origin, it may also be in liquid form.

DAO and compositions comprising DAO, to be used in the prevention or treatment of attention deficit hyperactivity disorder (ADHD), may be in the form of tablets, capsules or sachets containing DAO in free form, in powder, lyophilised powder, microcapsules, nanocapsules or liposomes of DAO with gastric protection.

DAO may also be mixed with caffeine to potentiate the effects of prevention and treatment of attention deficit hyperactivity disorder. Accordingly, a composition comprising DAO and caffeine is also disclosed herein.

Caffeine is an alkaloid of the xanthine group with stimulating properties that is used for the treatment of attention deficit hyperactivity disorder.

The DAO content of the present invention is between 0.1 and 50 mg per unit dose, preferably between 2 and 20 mg.

The caffeine content of the present invention is between 1 and 100 mg per unit dose, preferably between 5 and 50 mg.

DAO or compositions comprising DAO for the prevention and treatment of attention deficit hyperactivity disorder can be taken before, after or with meals.

The use of DAO or compositions comprising DAO of the present invention directly affects the blood histamine level and therefore the symptoms of attention deficit hyperactivity disorder as a consequence of accumulated histamine levels.

The DAO or compositions comprising DAO of the present invention are prepared from DAO in free form, in powder, lyophilised powder, microcapsules, nanocapsules or liposomes of DAO that have an enteric coating protecting the DAO from gastric acidity, so that these various forms can be filled directly into sachets or introduced into a capsule or compressed to give rise to tablets. The enteric coating layer that coats the various forms rapidly disintegrates or dissolves in a neutral or alkaline medium.

In the case of microgranules, the cores can be inert sugar-based cores or similar on which the DAO is applied, or these cores may already contain DAO mixed with other excipients. These excipients can be binders, surfactants, fillers, dispersants, alkaline additives or other pharmaceutically acceptable ingredients either alone or in a mixture. The binders can be cellulose-type such as hydroxypropyl methylcellulose, hydroxypropyl cellulose or carboxymethylcellulose sodium, polyvinylpyrrolidone, sugars, starches and other pharmaceutically acceptable substances with cohesive properties. Suitable surfactants are found in the groups of acceptable ionic or non-ionic surfactants such as, for example, sodium lauryl sulphate.

Alternatively, DAO can be mixed with alkaline compounds and additionally mixed with suitable constituents to be formulated into a core material. These core materials can be produced by extrusion/spheronisation or by compression using various processing equipment.

DAO can also be mixed with pharmaceutically acceptable alkaline substances such as salts of phosphoric acid and sodium, potassium, calcium, magnesium and aluminum, carbonic acid, citric acid or other suitably weak organic and inorganic acids; a co-precipitate of aluminum hydroxide/sodium bicarbonate; substances normally used in anti-acid preparations such as hydroxides of aluminum, calcium and magnesium; magnesium oxide or compound substances such as $Al_2O_3.6MgO.CO_2.12H_2O$, $(Mg_6Al_2(OH)_{16} CO_3.4H_2O$, $MgO.Al_2O_3.2SiO_2.nH_2O$ or similar compounds; pH buffering substances such as tris(hydroxymethyl)aminomethane, basic amino acids and their salts or other pharmaceutically acceptable pH buffering substances.

The enteric coating layers may contain pharmaceutically acceptable plasticisers to obtain the desired mechanical properties of flexibility and hardness. These plasticisers can be, for example, triacetin, citric acid esters, phthalic acid esters, cetyl alcohol, polyethylene glycols, polysorbates or other plasticisers.

The present invention also relates to a method of treatment comprising the administration to a patient, presenting with the symptoms of attention deficit hyperactivity disorder or with the risk of suffering from it, of DAO or a composition comprising DAO according to any of the embodiments of the present invention in a therapeutically effective amount.

EXAMPLES

Example 1

DAO tablets were prepared from microgranules containing 4% DAO, with the following formula:

| | |
|---|---|
| DAO | 4 mg |
| Mannitol | 40 mg |
| Microcrystalline cellulose | 25 mg |
| Hydroxypropyl cellulose | 10 mg |
| Corn starch | 10 mg |
| Citric acid | 6 mg |

The microgranules were coated with hydroxypropyl methylcellulose.

To make the tablets, the DAO microgranules were compressed with microcrystalline cellulose and sodium stearyl fumarate.

Example 2

DAO tablets were prepared from microgranules containing 4% DAO and 10% caffeine with the following formula:

| | |
|---|---|
| DAO | 4 mg |
| Caffeine | 10 mg |
| Mannitol | 35 mg |
| Microcrystalline cellulose | 15 mg |
| Hydroxypropyl cellulose | 10 mg |

-continued

| | |
|---|---|
| Hydroxypropyl methylcellulose | 10 mg |
| Ascorbic acid | 6 mg |

The microgranules were coated with a copolymer of methacrylic acid.

To make the tablets, the microgranules of DAO were compressed with microcrystalline cellulose and magnesium stearate.

Example 3

DAO sachets were prepared containing 100 or 150 mg of DAO microgranules prepared as in the first part of example 1.

Example 4

DAO and caffeine sachets were prepared containing 100 or 150 mg of DAO microgranules prepared as in the first part of example 2.

Example 5

DAO capsules were prepared containing 100 or 150 mg of DAO microgranules prepared as in the first part of example 1, filling the soft gelatin capsules with these microgranules.

Example 6

DAO and caffeine capsules were prepared, containing 100 or 150 mg of the DAO microgranules prepared as in the first part of example 2, filling the soft gelatin capsules with these microgranules.

Example 7

Determination of the efficacy of DAO compositions, the object of the present invention, in children with a diagnosis of attention deficit hyperactivity disorder and who present with DAO deficiency.

The study was carried out with 60 children selected with ages of between 8/10 years to 18 years, diagnosed with attention deficit hyperactivity disorder, as out-patients. Of these 60, 45 were boy and 15 girls, since girls often only present symptoms of attention deficit whereas hyperactivity is more common in boys.

Before starting treatment with DAO administration, the children were selected using the results of DAO activity level in plasma. Reduced DAO activity was considered to be between 80 and 40 HDU/ml and very reduced activity was below 40 HDU/ml. Therefore, those children with reduced DAO values, that is, below 80 HDU/ml, were included in the study, although the symptoms of ADHD were most clearly seen in children with DAO activity below 60 HDU/ml. Of the 60 children with ADHD diagnosis participating in the study, 78% showed activity below the threshold of normal (80 HDU/ml) and 39% showed activity below 40, that is had "very reduced" activity. Therefore, of the 100% of children diagnosed, 78% participated in the study whereas the other 22% had ADHD originating in other causes.

Oral compositions containing DAO, alone or associated with caffeine, object of the present invention, were tested in a total of 47 children selected with ages between 8/10 years to 18 years, diagnosed with attention deficit hyperactivity disorder, as out-patients. Of these 47, 36 were boys and 11 girls, and they were randomly assigned to receive compositions of DAO, DAO and caffeine or placebo.

In addition to DAO treatment, milk was removed from the diet of the children participating in the study; this is a food consumed daily and recurrently that contains histamine and other milk proteins that cause endogenous release of histamine, so that ingestion of additional DAO is more efficient if an important source of histamine such as milk is removed at the same time.

Methods based on school performance were used for evaluation of treatment. Children with a diagnosis of ADHD have poor performance in school and, when through treatment they reduce hyperactivity and recover attention, they clearly improve their school results in both academic results and attitude.

The table below was used to quantify the result of treatment: "Child Attention Profile" (CAP) diagnostic evaluation scale that is based on the observation and scoring of 12 items (Cozza S. J. y col., Tratamiento de Niños y Adolescentes, Tomo II, capitulo XXXIII, 1399-1452 en Hales R E, Yudosfky S C (ed), Tratamiento de Psiquiatría Clínica, Barcelona Masson 2004) [Cozza S. J. et al., Treatment of Children and Adolescents, Volume II, Chapter XXXIII, 1399-1452 in Hales R E, Yudosfky S C (ed,), Clinical Psychiatric Treatment, Barcelona Masson 2004]:

| Child Attention Profile (CAP) | | | |
|---|---|---|---|
| | False | Occasionally | Frequently |
| 1 Fails to finish things he/she starts | | | |
| 2 Can't concentrate, can't pay attention for long | | | |
| 3 Can't sit still, restless, or hyperactive | | | |
| 4 Fidgets | | | |
| 5 Daydreams or gets lost in their thoughts | | | |
| 6 Impulsive or acts without thinking | | | |
| 7 Difficulty in following directions | | | |
| 8 Talks out of turn | | | |
| 9 Messy work | | | |
| 10 Inattentive, easily distracted | | | |
| 11 Talks too much | | | |
| 12 Fails to carry out assigned tasks | | | |

The 12 items are scored 0, 1, 2. The total score is the sum of all the items.

Sub-scores: Lack of attention (sum of scores of items 1,2,5,7,9,10 and 12); Hyperactivity (sum of scores of items 3,4,6,8,11).

Recommended scores as an upper limit of normality (percentile 93)

| | Boys | Girls |
|---|---|---|
| Lack of Attention | 9 | 7 |
| Hyperactivity | 6 | 5 |
| Total score | 15 | 11 |

The "Abbreviated Conners" questionnaire was also used:

| | Not at all | Just a little | Pretty much | Very much |
|---|---|---|---|---|
| 1 Restless or overactive | | | | |
| 2 Excitable, impulsive | | | | |

-continued

|   | | Not at all | Just a little | Pretty much | Very much |
|---|---|---|---|---|---|
| 3 | Disturbs other children | | | | |
| 4 | Fails to finish things he/she starts | | | | |
| 5 | Constantly fidgeting | | | | |
| 6 | Inattentive, easily distracted | | | | |
| 7 | Demands must be met immediately, easily frustrated | | | | |
| 8 | Cries often and easily | | | | |
| 9 | Mood changes quickly and drastically | | | | |
| 10 | Temper outbursts, explosive and unpredictable behaviour | | | | |

The Connors behavioural questionnaire for parents is a guideline for recording the most significant hyperactive behaviours that may be shown in possible attention disorders, which must be completed by parents, enabling them to also have a degree of clarity into minor problems. It consists of 10 items that must be completed with a score of 0 to 3 points; with 0 corresponding to the absence of the observed item in the person being evaluated and the value 3 for constant and common presence. The maximum score is 30. Between 0 to 10 points: normally active, does not have problems; from 10 to 20 points: situational hyperactivity or normally active but immature in temperament; from 20 to 30 points: very hyperactive or disruptive. In general terms, for boys between 6 and 11 years, ADHD is suspected with a score higher than 16 points. For girls between 6 and 11 years, ADHD is suspected with a score higher than 12 points.

The following tables show the results of reduction of symptoms caused by ADHD after the administration of a dosage protocol of 4 mg DAO twice a day to 37 children diagnosed with ADHD and with DAO deficiency compared to 10 children who were administered placebo.

TABLE 1

Comparative results of observation and scoring the 12 items of the "Child Attention Profile" (CAP) between children who took DAO tablets, of Example 1, and those who did not take DAO. These results show a clear improvement in the attention profile of treated children, both boys and girls, in comparison to the results obtained after placebo administration.

|   |   | Initial profile | Final profile |
|---|---|---|---|
| Boys with DAO of Example 1 | Lack of attention | 10-14 | 6-9 |
|  | Hyperactivity | 8-10 | 4-6 |
|  | Total | 18-24 | 10-15 |
| Boys with placebo | Lack of attention | 10-14 | 10-13 |
|  | Hyperactivity | 8-10 | 7-10 |
|  | Total | 18-24 | 14-23 |
| Girls with DAO of Example 1 | Lack of attention | 9-14 | 5-7 |
|  | Hyperactivity | 7-10 | 3-5 |
|  | Total | 16-24 | 8-12 |
| Girls with placebo | Lack of attention | 9-14 | 8-14 |
|  | Hyperactivity | 7-10 | 7-9 |
|  | Total | 16-24 | 15-23 |

TABLE 2

Comparative results of the observation and scoring of the 10 items of the "Abbreviated Conners" questionnaire between children taking DAO tablets, of Example 1, and those that did not take DAO. These results show a clear improvement in the attention profile of treated children, both boys and girls, in comparison to the results obtained after placebo administration.

|   | Initial score | Final score |
|---|---|---|
| Boys with DAO of Example 1 | 16-30 | 8-15 |
| Girls with DAO of Example 1 | 12-30 | 6-12 |
| Boys with placebo | 16-30 | 15-29 |
| Girls with placebo | 13-30 | 12-27 |

TABLE 3

Comparative results of the observation and scoring of the 10 items of the "Abbreviated Conners" questionnaire between children taking DAO and caffeine tablets, of Example 2, and those who did not take DAO. These results show a clear improvement in the attention profile of treated children, both boys and girls, in comparison to the results obtained after placebo administration.

|   | Initial score | Final score |
|---|---|---|
| Boys with DAO and caffeine of Example 2 | 16-29 | 7-14 |
| Girls with DAO and caffeine of Example 2 | 12-28 | 5-10 |
| Boys with placebo | 16-29 | 15-29 |
| Girls with placebo | 13-27 | 12-27 |

The invention claimed is:

1. A method of treating attention deficit hyperactivity disorder (ADHD) in a human, the method comprising:
    testing diamine oxidase (DAO) activity level in plasma of the human;
    responsive to results of the testing being less than or equal to a pre-defined threshold, orally administering a dosage of 0.1-50 mg of DAO to the human; and
    wherein the pre-defined threshold is not greater than 80 HDU/ml.

2. The method according to claim 1, wherein the DAO is administered in at least one of tablets, capsules, and sachets.

3. The method according to claim 1, wherein the dosage is 2-20 mg.

4. The method according to claim 1, further comprising administering caffeine to the human.

5. The method according to claim 4, wherein a dosage of the administered caffeine is 1-100 mg.

6. The method according to claim 1, wherein the administered DAO is provided with gastric protection.

7. The method according to claim 1, wherein a form of the administered DAO is selected from the group consisting of free form, powder, lyophilised powder, microcapsules, nanocapsules, and liposomes.

8. The method according to claim 1, wherein the DAO is included in a composition.

9. The method according to claim 5, wherein the dosage of the administered caffeine is 5-50 mg.

10. The method according to claim 8, wherein the composition has an enteric coating that protects the DAO from gastric acidity.

* * * * *